(12) United States Patent  
Bhalla et al.

(10) Patent No.: US 9,238,030 B2
(45) Date of Patent: Jan. 19, 2016

(54) METHODS FOR TREATMENT OF DISEASES AND DISORDERS RELATED TO TRANSDUCIN β-LIKE PROTEIN 1 (TBL1) ACTIVITY, INCLUDING MYELOPROLIFERATIVE NEOPLASIA AND CHRONIC MYELOID LEUKEMIA

(71) Applicant: Beta Cat Pharmaceuticals, LLC, Gaithersburg, MD (US)

(72) Inventors: Kapil N. Bhalla, Kansas City, KS (US); Stephen Horrigan, Gaithersburg, MD (US)

(73) Assignee: Beta Cat Pharmaceuticals, Inc., Gaithersburg, MD (US)

( * ) Notice: Subject to any disclaimer, the term of this patent is extended or adjusted under 35 U.S.C. 154(b) by 264 days.

(21) Appl. No.: 13/670,377

(22) Filed: Nov. 6, 2012

(65) Prior Publication Data

US 2013/0143920 A1 Jun. 6, 2013

Related U.S. Application Data

(60) Provisional application No. 61/556,245, filed on Nov. 6, 2011.

(51) Int. Cl.
*A61K 31/15* (2006.01)
*A61K 31/445* (2006.01)
*A61K 31/4545* (2006.01)
*A61K 38/17* (2006.01)

(52) U.S. Cl.
CPC .............. *A61K 31/4545* (2013.01); *A61K 31/15* (2013.01); *A61K 38/17* (2013.01); *A61K 31/445* (2013.01)

(58) Field of Classification Search
CPC .............................. A61K 31/15; A61K 31/445
See application file for complete search history.

(56) References Cited

U.S. PATENT DOCUMENTS

2011/0034441 A1 2/2011 Hood et al.

FOREIGN PATENT DOCUMENTS

| WO | WO 2008140792 A1 * | 11/2008 |
|----|----|----|
| WO | WO 2008/147713 | 12/2008 |
| WO | WO2010059142 A1 | 5/2010 |
| WO | WO 2011/025685 | 3/2011 |
| WO | WO 2011/038467 | 4/2011 |

OTHER PUBLICATIONS

Wang et al. Science, 2010, vol. 327, pp. 1650-1653.*
Mandawat et al. Blood, 2010, vol. 116, No. 24, pp. 5306-5315.*
Braekeleer et al. Annals of Hematology, 2010. vol. 89, No. 10. pp. 1277-1281.*
International Search Report from related application PCT/US2012/63746, dated Jan. 23, 2013.
Written Opinion of the International Searching Authority from related application PCT/US2012/63746, dated Jan. 23, 2013.
Thielen, N. et al. "New insights into the pathogenesis of chronic myeloid leukemia: towards a path to cure" Neth. J. Med. Oct. 2011, vol. 69, Issue 10, pp. 430-440.
Li J. et al. "TBL1-TBL1R and [beta]-catenin recruit each other to Wnt target-gene promoter for transcription activation and oncogenesis" Nat. Cell Biol. Feb. 2008, vol. 10, Issue 2, 160-169.
PCT International Preliminary Report on Patentability, issued in International Application No. PCT/US2012/063746, dated May 6, 2014.
"BC2059—An inhibitor of the WNT/Beta Catenin Pathway", Financing Executive Summary, Beta Cat Pharmaceuticals, LLC, 2010. Downloaded from http://www.pharmaconnections.com/Investment_Opps/BetaCat_OLD/Beta_Cat_BC2059_Executive_Summary.pdf on Jan. 27, 2015.
Bhalla et al., "Anti-AML activity of a novel beta-catenin antagonist BC2059", *J Clin Oncol.*, 30: Abstract 10605, 2012.
Extended European Search Report issued in European Application No. 12845590.4, dated Feb. 10, 2015.
Fiskus et al., "65. Treatment with beta-catenin antagonist BC2059 exerts single agent efficacy and exerts improved activity with tyrosine kinase inhibitor (TKI) or pan-histone deacetylase (HDAC) inhibitor against human CML and myeloproliferative neoplasm (MPN) progenitor cells", *Blood, 53rd Annual Meeting and Exposition of the American Society of Hematology (ASH)*, 118(21): 31, 2011.
Fisku s et al., "Abstract C144: Treatment with β-catenin antagonist BC2059 exhibits single agent efficacy and exerts superior activity with tyrosine kinase inhibitor (TKI) or histone deacetylase (HDAC) inhibitor against human AML, CML, and myeloproliferative neoplasm (MPN) progenitor cells", *Molecular Cancer Therapeutics*, 10(S1): C144, 2011.
Kosugi et al., "Histone deacetylase inhibitors are the potent inducer/enhancer of differentiation in acute myeloid leukemia: A new approach to anti-leukemia therapy", *Leukemia*, 13(9): 1316-1324, 1999.
Anastas and Moon, "WNT signaling pathways as therapeutic targets in cancer", *Nat Rev Cancer*, 13: 11-26, 2013.
Clevers and Nusse, "Wnt/b-catenin signaling and disease", *Cell*, 149: 1192-1205, 2012.
Coluccia et al., "Bcr-Abl stabilizes beta-catenin in chronic myeloid leukemia through its tyrosine phosphorylation", *EMBO J.*, 26:1456-66, 2007.
Cruciat, "Caesin kinase 1 and Wnt/b-catenin signaling", *Curr Opin Cell Biol.*, 31: 46-55, 2014.
Curtin and Lorenzi, "Drug discovery approaches to target Wnt signaling in cancer stem cells", *Oncotarget*, 1: 52-66, 2010.
Dimitrova et al., "Direct ubiquitination of beta-catenin by Siah-1 and regulation by the exchange factor TBL1", *J Biol Chem.*, 285:13507-16, 2010.

(Continued)

*Primary Examiner* — Samira Jean-Louis
(74) *Attorney, Agent, or Firm* — Parker Highlander PLLC (57) ABSTRACT

Methods for treatment of diseases and disorders related to transducin β-like protein 1 (TBL1) activity, including myeloproliferative neoplasia, chronic myeloid leukemia, and acute myeloid leukemia.

20 Claims, 10 Drawing Sheets

(56) References Cited

OTHER PUBLICATIONS

Fiskus et al., "Pre-clinical efficacy of combined therapy with novel β-catenin antagonist BC2059 and histone deacetylase inhibitor against AML cells", *Leukemia*. Dec. 8, 2014.

Gehrke et al., "Targeting the WNT/beta-catenin/TCF/LEF1 axis in solid and haematological cancers: Multiplicity of therapeutic options", *Eur J Cancer.*, 45:2759-67, 2009.

Hoffmeyer et al., "Wnt/bcatenin signaling regulates telomerase in stem cells and cancer cells", *Science*, 336: 1549-54, 2012.

Kahn, "Can we safely target the WNT pathway?", *Nat Rev Drug Discov.*, 13: 513-32, 2014.

Kajiguchi et al., "FLT3 regulates beta-catenin tyrosine phosphorylation, nuclear localization, and transcriptional activity in acute myeloid leukemia cells", *Leukemia*, 21:2476-84, 2007.

Kajiguchi et al., "Y654 of β-catenin is essential for FLT3/ITD-related tyrosine phosphorylation and nuclear localization of β-catenin", *Eur J Haematol.*, 88:314-20, 2012.

Kode et al., "Leukemogenesis induced by an activating b-catenin mutation in osteoblasts" *Nature*, 506; 240-44, 2014.

Lane et al., "Differential niche and Wnt requirements during acute myeloid leukemia progression", *Blood*, 118:2849-56, 2011.

Li et al., "Wnt signaling through inhibition of b-catenin degradation in an intact axinl complex", *Cell*, 149: 1245-56, 2012.

Minke et al., "Small molecule inhibitors of WNT signaling effectively induce apoptosis in acute myeloid leukemia cells", *Eur J Haematol.*, 82:165-75, 2009.

Mosimann et al., "β-catenin hits chromatin: regulation of Wnt target gene activation", *Nat Rev Mol Cell Biol.*, 10: 276-86, 2009.

Niehrs, "The complex world of WNT receptor signaling", *Nat Rev Mol Cell Biol*, 13: 767-79, 2012.

Oberoi et al., "Structural basis for the assembly of the SMRT/NCoR core transcriptional repression machinery", *Nat Struct Mol Biol.*, 18:177-84, 2011.

Perissi et al., "TBL1 and TBLR1 phosphorylation on regulated gene promoters overcomes dual CtBP and NCoR/SMRT transcriptional repression checkpoints", *Mol Cell.*, 29: 755-66, 2008.

Saha et al., "Combined Targeting of β-Catenin and FLT-3 Is Synergistically Lethal Against Cultured and Primary AML Blast Progenitor Cells Expressing FLT3 Internal Tandem Duplication (ITD)", *Blood*, 124: 618, 2014.

Schneider et al., "Role of casein kinase 1A1 in the biology and targeted therapy of del(5q) MDS", *Cancer Cell*, 26: 509-20, 2014.

Takahashi-Yanaga and Kahn, "Targeting WNT signaling: can we safely eradicate cancer stem cells", *Clin Cancer Res.*, 16:3153-62, 2010.

Valencia et al., "Wnt signaling pathway is epigenetically regulated by methylation of Wnt antagonists in acute myeloid leukemia", *Leukemia*, 23(9):1658-66, 2009.

Xeuling and Wang, "Role of Wnt canonical pathway in hematologic malignancies", *J Hematol Oncol.*, 3: 33-39, 2010.

Yeung et al., "β-catenin mediates the establishment and drug resistance of MLL leukemia stem cells", *Cancer Cell*, 18: 606-18, 2010.

\* cited by examiner

* Indicates values significantly greater than treatment with either agent alone p< 0.01

FIG. 2

| Cells and treatment | % of cells | | |
|---|---|---|---|
| K-562 | G0/G1 | S | G2/M |
| Untreated | 42.6 ± 0.1 | 35.4 ± 1.6 | 22.1 ± 1.7 |
| 10 nM BC2059 | 45.5 ± 0.6 | 33.4 ± 0.6 | 21.1 ± 0.8 |
| 20 nM BC2059 | 45.8 ± 1.4 | 34.7 ± 1.3 | 19.8 ± 0.9 |
| 50 nM BC2059 | 49.2 ± 1.4 | 28.2 ± 0.9 | 22.5 ± 1.3 |

FIG. 3A

| Cells and treatment | % of cells | | |
|---|---|---|---|
| LAMA-84 | G0/G1 | S | G2/M |
| Untreated | 43.9 ± 4.8 | 41.8 ± 4.5 | 14.3 ± 0.3 |
| 10 nM BC2059 | 42.0 ± 5.1 | 43.7 ± 6.1 | 14.3 ± 1.3 |
| 20 nM BC2059 | 48.5 ± 4.6 | 37.9 ± 5.1 | 13.5 ± 1.3 |
| 50 nM BC2059 | 52.5 ± 0.8 | 34.5 ± 0.5 | 13.0 ± 0.9 |

* Indicates values significantly greater than treatment with either agent alone p<0.01

METHODS FOR TREATMENT OF DISEASES AND DISORDERS RELATED TO TRANSDUCIN β-LIKE PROTEIN 1 (TBL1) ACTIVITY, INCLUDING MYELOPROLIFERATIVE NEOPLASIA AND CHRONIC MYELOID LEUKEMIA

FIELD OF THE INVENTION

The present invention relates to the field of therapeutic methods and uses thereof to modulate diseases and disorders related to transducin β-like protein 1 (TBL1) activity, including myeloproliferative neoplasia, chronic myeloid leukemia and acute myeloid leukemia.

BACKGROUND OF THE INVENTION

Cancer is the second leading cause of death in the United States. It presents complex challenges for the development of new therapies. Cancer is characterized by the abnormal growth of malignant cells that have undergone a series of genetic changes that lead to growth of tumor mass and metastatic properties.

Transducin β-like protein 1 (TBL1) family of proteins has been shown to be involved in the transcriptional activator by acting as a co-regulator exchange factor. The TBL1 family is composed of TBL1X, TBL1Y and TBLR1 proteins. These proteins are components of the SMRT-nuclear receptor/co-repressor (N-CoR) complex where they act to exchange the co-repressors and co-activators on the complex. SMRT and NCoR are large co-repressor proteins that are involved in the transcriptional repression by many different nuclear receptors. TBL1 family of proteins forms a reversible complex with NCoR/SMRT to act as a transcriptional activator for nuclear receptors.

Beta-catenin (β-catenin) is part of a complex of proteins that constitute adherens junctions (AJs). AJs are necessary for the creation and maintenance of epithelial cell layers by regulating cell growth and adhesion between cells. β-catenin also anchors the actin cytoskeleton and may be responsible for transmitting the contact inhibition signal that causes cells to stop dividing once the epithelial sheet is complete.

Wnt/β-catenin pathway has been shown to play a role in cancer. Recent studies have shown that TBL1 is able to bind to β-catenin and recruit the complex to Wnt responsive promoters to activate specific transcriptional program. It has also been shown that TBL1 is required for β-catenin to actively transcribe target genes. Further, TBL1 appears to protect β-catenin from ubiquitination (a post-translational modification by certain enzymes) and degradation. However, the mechanism of the interaction between TBL1 and β-catenin is unknown.

Aberrant β-catenin signaling plays a important role in tumorigenesis. In particular, colorectal cancer is estimated to have greater than 80% mutations in the β-catenin pathway, leading to unregulated oncogenic signaling. Aberrant β-catenin signaling has been shown to be involved in various cancer types, including melanoma, breast, lung, liver, gastric, myeloma, and acute myeloid leukemia (AML). Further, aberrant Wnt/β-catenin signaling has been found in a large number of other disorders, including osteoporosis, osteoarthritis, polycystic kidney disease, diabetes, schizophrenia, vascular disease, cardiac disease, hyperproliferative disorders, and neurodegenerative diseases. Myeloproliferative neoplasms (MPNs) are a closely related group of hematological malignancies in which the bone marrow cells that produce the body's blood cells develop and function abnormally. The three main myeloproliferative neoplasms are Polycythemia Vera (PV), Essential Thrombocythemia (ET) and Primary Myelofibrosis (PMF). A gene mutation in JAK2 is present in most PV patients and 50% of ET and PMF patients. The beta catenin pathway is activated in MPN in many cases and required for survival of these cells.

Chronic Myeloid Leukemia is a form of leukemia characterized by the increased and unregulated growth of predominantly myeloid cells in the bone marrow and the accumulation of these cells in the blood that contain the "Philadelphia chromosome", where a piece of chromosome 9 and a piece of chromosome 22 break off and trade places to form the bcr-abl fusion gene. CML has activation of several other oncogenic pathways including the beta catenin pathway which is required for CML cell growth.

Accordingly, there is a need for agents that are able interrupt the Wnt/β-catenin pathway and inhibit the deregulated activity of this pathway for the treatment, diagnosis and prevention of β-catenin pathway-related disorders and diseases.

SUMMARY OF THE INVENTION

The present invention provides methods for treating disease or disorders by administering a therapeutically effective amount of an agent that inhibits transducin β-like protein 1 (TBL1) from binding disease-associated molecules. In particular, the provided methods and compositions relate to the treatment, diagnosis, and/or prevention of β-catenin signaling pathway disorders.

In another preferred embodiment, the β-catenin related disorder includes myeloproliferative neoplasia (MPN), chronic myeloid leukemia (CML) and acute myeloid leukemia (AML).

In the most preferred embodiment, the provided agent has the following structure:

or a pharmaceutically acceptable salt thereof. This agent is referred to as Compound 1 throughout this application.

In a preferred embodiment, TBL1 is selected from the group consisting of transducin (beta)-like 1X-linked (TBL1X), transducin (beta)-like 1Y-linked (TBL1Y) and transducin (beta)-like R1-linked TBLR1 proteins.

In one embodiment, the activator is beta-catenin.

In another embodiment, the activator is a beta-catenin related protein.

In another embodiment, the provided agent can be used in combination with other therapeutic agents, including but not limited to tyrosine kinase inhibitor (including but not limited to nilotinib), histone deacetylase inhibitor (including, but not limited to panobinostat), other anti-cancer agents and other therapeutic agents.

DETAILED DESCRIPTION OF THE INVENTION

Definitions

The following definitions are used, unless otherwise described.

The term "prodrugs" refers to compounds, including but not limited to monomers and dimers of the compounds of the invention, which become under physiological conditions compounds of the invention or the active moieties of the compounds of the invention.

The term "active moieties" refers to compounds which are pharmaceutically active in vivo, whether or not such compounds are compounds of the invention.

The term "subject" includes mammals, including humans. The terms "patient" and "subject" are used interchangeably.

The term "Myeloproliferative Neoplasias" or "MPN" refers to a closely related group of hematological malignancies in which the bone marrow cells that produce the body's blood cells develop and function abnormally. The three main myeloproliferative neoplasms are Polycythemia Vera, Essential Thrombocythemia and Primary Myelofibrosis.

The term "Chronic Myeloid Leukemia" or "CML" refers to a cancer of the white blood cells. It is a form of leukemia characterized by the increased and unregulated growth of predominantly myeloid cells in the bone marrow and the accumulation of these cells in the blood that contain the "Philadelphia chromosome", where a piece of chromosome 9 and a piece of chromosome 22 break off and trade places to form the bcr-abl fusion gene.

The term "Acute Myeloid Leukemia" or "AML" refers to a cancer of the blood and bone marrow.

The term "TG101209" refers to a JAK2 inhibitor which is an orally bioavailable, small molecule, ATP-competitive inhibitor towards several tyrosine kinases. This compound is also known as N-tert-butyl-3-[[5-methyl-2-[4-(4-methylpiperazin-1-yl)anilino]pyrimidin-4-yl]amino]benzenesulfonamide.

The term "therapeutically effective amount" means the amount of a compound that, when administered to a subject for treating a disease or disorder, is sufficient to effect such treatment for the disease or disorder. The "therapeutically effective amount" can vary depending on the variety of factors, including the compound, the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In one embodiment, the terms "treating" or "treatment" refer to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences*, 1977, 66: 1 et seq.

Pharmaceutically acceptable salts include, but are not limited to, acid addition salts. For example, the nitrogen atoms may form salts with acids. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid.

Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Description of the Invention

The present invention provides methods for treating disease or disorders by administering a therapeutically effective amount of an agent that inhibits transducin β-like protein 1 (TBL1) from binding disease-associated molecules. In particular, the provided methods and compositions relate to the treatment, diagnosis, and/or prevention of β-catenin signaling pathway disorders in Myeloproliferative Neoplasia (MPN), Chronic Myeloid Leukemia (CML), and Acute Myeloid Leukemia (AML).

In one aspect, the present invention is directed to a method of treating and/or preventing a β-catenin related disorder comprising administering to a patient in need thereof a therapeutically effective amount of an agent that binds to the transducin β-like protein 1 (TBL1) protein thereby preventing binding of β-catenin.

In the most preferred embodiment, the provided agent has the following structure:

or a pharmaceutically acceptable salt thereof. This compound is referred to as "Compound 1" throughout the application.

In another preferred embodiment, the β-catenin related disorder includes cancer, including but not limited to MPN, CML, and AML.

In a preferred embodiment, TBL1 is selected from the group consisting of transducin (beta)-like 1X-linked (TBL1X), transducin (beta)-like 1Y-linked (TBL1Y) and transducin (beta)-like R1-linked TBLR1 proteins.

Compound 1 was originally identified in a cell based screen for its ability to inhibit the transcriptional activation or β-catenin genes. Characterization of this compound led to the discovery that the compound is able to induce the degradation of β-catenin, interfere with the transcriptional activation complex, and has characteristics of a nuclear receptor signaling pathway modulator. Compound 1 interacts with TBL1 and prevents β-catenin from associating with TBL1 and leads to beta catenin degradation.

This activity of Compound 1 was found to inhibit the beta catenin pathway in cancer cells and cause those cells to undergo apoptosis. Specifically, cell lines derived from CML patients and cell lines and primary cells derived from MPN patients undergo apoptosis and growth inhibition in the presence of Compound 1. In addition, the activity of Compound 1 is synergistic with compounds that affect therapeutically important signaling pathways in these diseases (such as JAK2, BCR-ABL, and HDACs) and can be used in combination with these agents to ameliorate these diseases in individuals with the disease.

Thus, in some embodiments, the provided agents can be used in combination with other therapeutic agents, including but not limited to tyrosine kinase inhibitor (including but not limited to nilotinib), histone deacetylase inhibitor (including, but not limited to panobinostat), other anti-cancer agents and other therapeutic agents.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The total daily dose of the compounds of this invention administered to a human or lower animal may range from about 0.0001 to about 1000 mg/kg/day. If desired, the effective daily dose can be divided into multiple doses for purposes of administration; consequently, single dose compositions may contain such amounts or submultiples thereof to make up the daily dose.

For a clearer understanding of the invention, details are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Example 1

Activity of Compound 1 on MPN Cells in Inducing Apoptosis

Figure 1A:
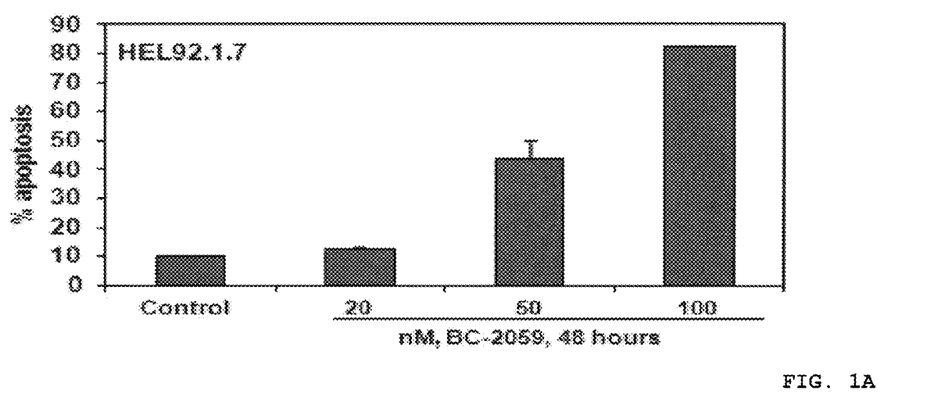
FIGS. 1A-1D are bar charts that depict the activity of Compound 1 by itself and in combination with TG101209 on MPN cells in inducing apoptosis.
Figure 1B:
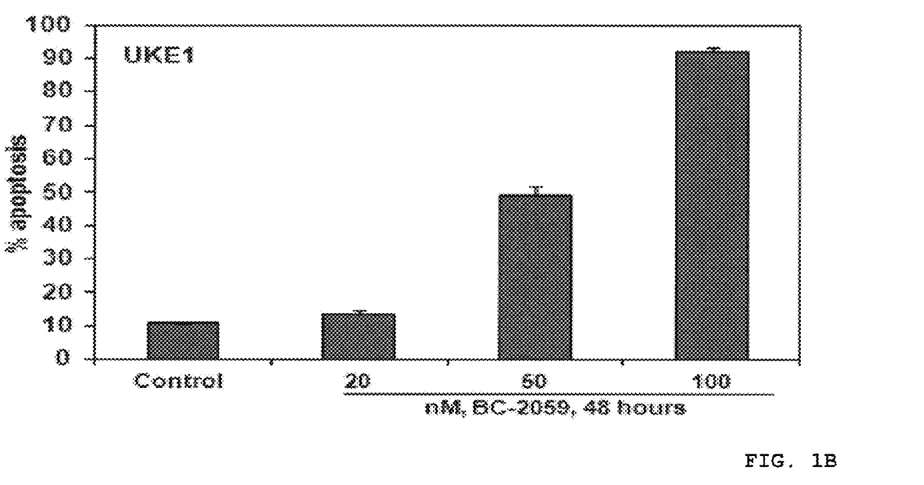
Figure 1C:
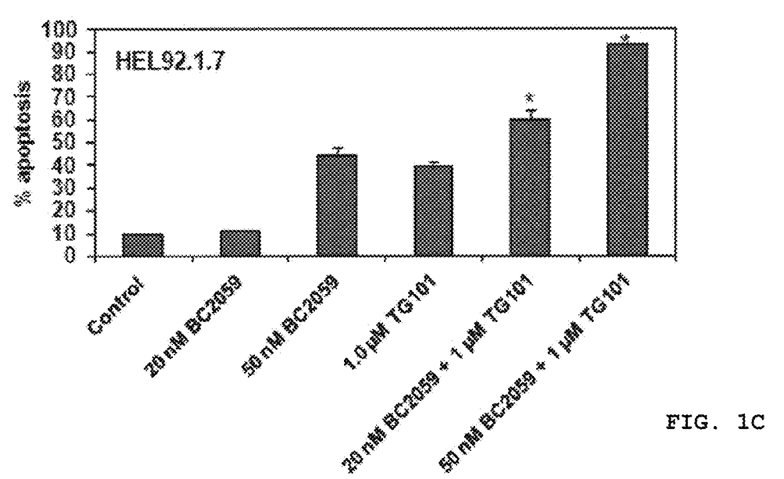
Figure 1D:
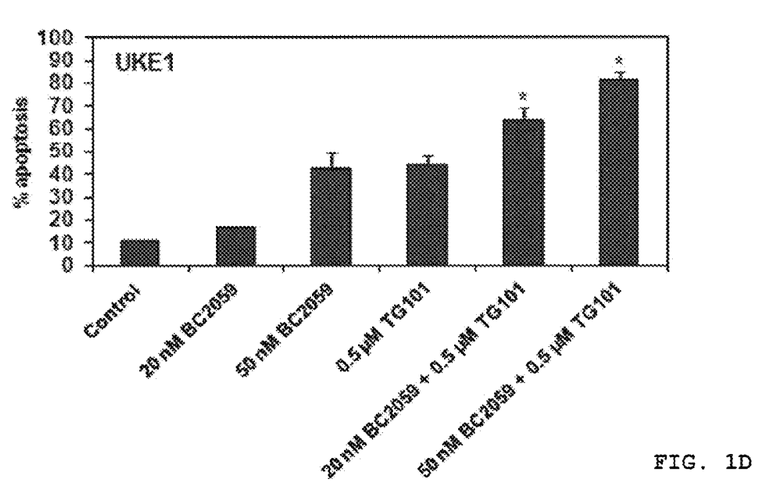

Briefly, the cell lines HEL 92.1.7 (FIGS. 1A and 1C) and UKE1 (FIGS. 1B and 1D) were seeded in medium containing 10% FBS and penicillin/streptomycin. After 24 hours, the cells were treated with either: 1) Compound 1; or 2) Compound 1 in combination with TG101209 for 48 hours. At the end of treatment, cells were washed with 1×PBS and stained with annexin V and TOPRO3 iodide. The percentages of apoptotic cells were determined by flow cytometry.

As FIGS. 1A-1D demonstrate, Compound 1 (referred to as BC2059 in Figures' legends) was induced apoptosis of both HEL 92.1.7 and UKE1 cells. These apoptosis-inducement effect was enhanced by TG101209.

Example 2

Activity of Compound 1 on Primary MPN Cells Isolated from Patients in Inducing Apoptosis and in Combination with Other Agents Briefly, the CD34+ cells isolated from bone marrow of MPN patients, were seeded in medium containing 10% FBS and penicillin/streptomycin. After 24 hours, the cells were treated with Compound 1 for 48 hours or Compound 1 in combination with TG101209. At the end of treatment, cells were washed with 1×PBS and stained with annexin V and TOPRO3 iodide. The percentages of apoptotic cells were determined by flow cytometry. Combination index (CI) was determined using the method of Chou-Talalay (Adv. Enzyme Regul. 22, 27-55).

Figure 2:
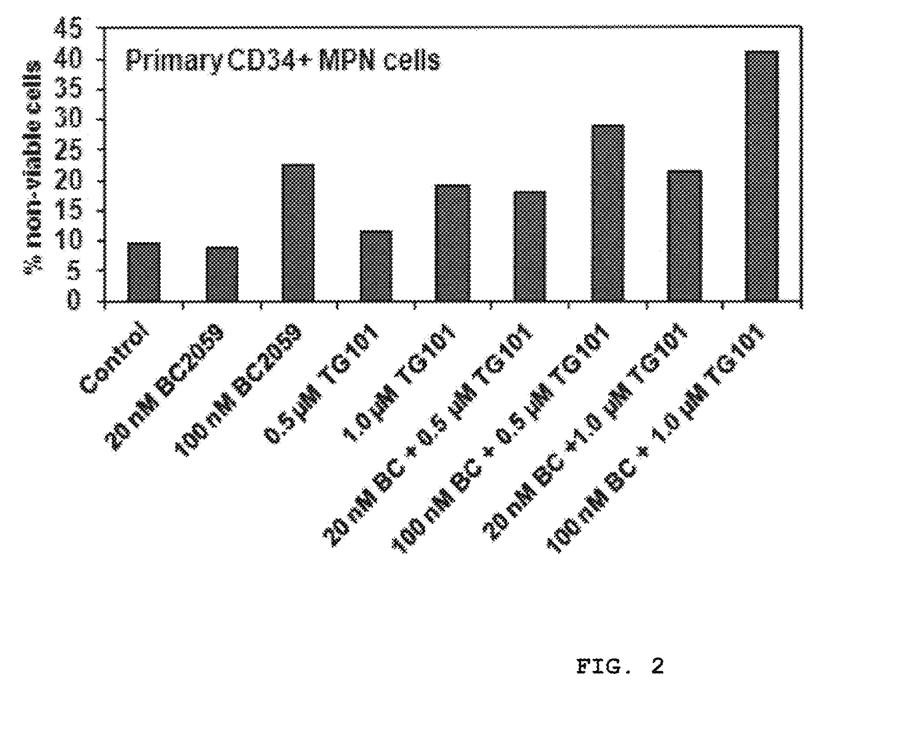
FIG. 2 is a bar chart that depicts the activity of Compound 1 by itself and in combination with TG101209 on primary MPN cells isolated from patients in inducing apoptosis.

FIG. 2 is a bar chart that depicts the results of this experiment. As one can see, Compound 1 (referred to as BC2059 in the Figure's legend) at 100 nM or above induced apoptosis of CD34+ MPN cells. The addition of TG101209 enhanced this effect.

Example 3

Activity of Compound 1 on CML Cells in Inducing Apoptosis

Briefly, cell lines K562 (human immortalized myelogenous leukemia line) and LAMA-84 (a human leucocytic cell line) were seeded in medium containing 10% FBS and penicillin/streptomycin. After 24 hours, the cells were treated with Compound 1 for 48 hours. At the end of the treatment, the cells were washed with 1×PBS and stained with annexin V and TOPRO3 iodide. The percentages of apoptotic cells were determined by flow cytometry.

Figure 3A:
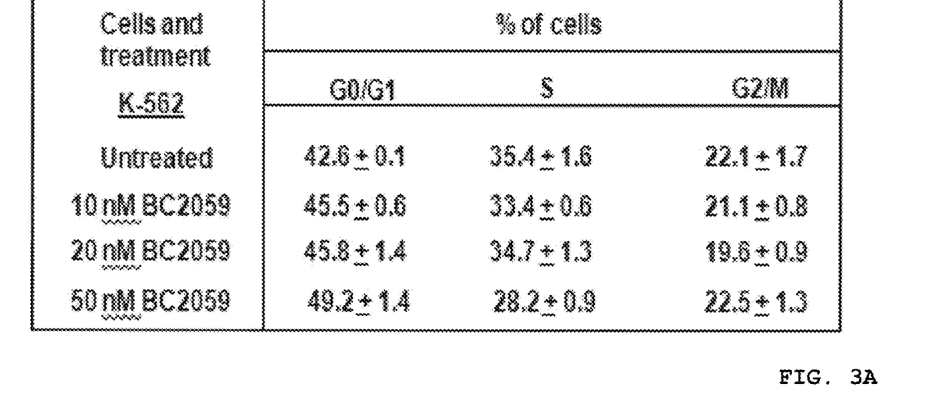
FIGS. 3A and 3B are tables which demonstrate the activity of Compound 1 on CML cells in inducing apoptosis.
Figure 3B:
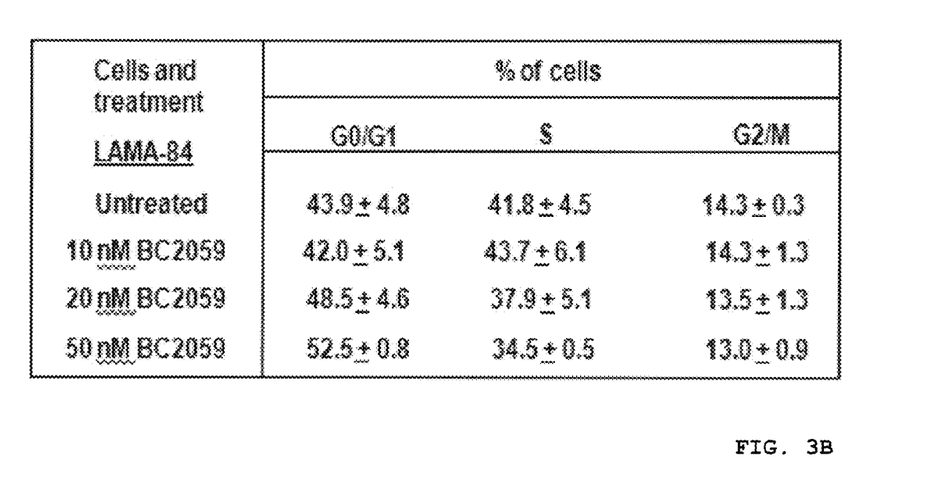

FIGS. 3A and 3B are tables which demonstrate the results of this experiment. As one can see, treatment with Compound 1 increased the number of apoptotic cells at G0/G1 phase of the cell cycle but did not have significant effect at S or G2/M phases of the cell cycle.

Example 4

Activity of Compound 1 on CML Cells in Inducing Apoptosis in Combination with Other Agents Briefly, the cell lines K562 and LAMA-84, were seeded in medium containing 10% FBS and penicillin/streptomycin. After 24 hours, the cells were treated with either: 1) Compound 1 alone; or 2) in combination with panobinostat and nilotinib for 48 hours. At the end of treatment, cells were washed with 1×PBS and stained with annexin V and TOPRO3 iodide. The percentages of apoptotic cells were determined by flow cytometry.

Figures 4A, 4C:
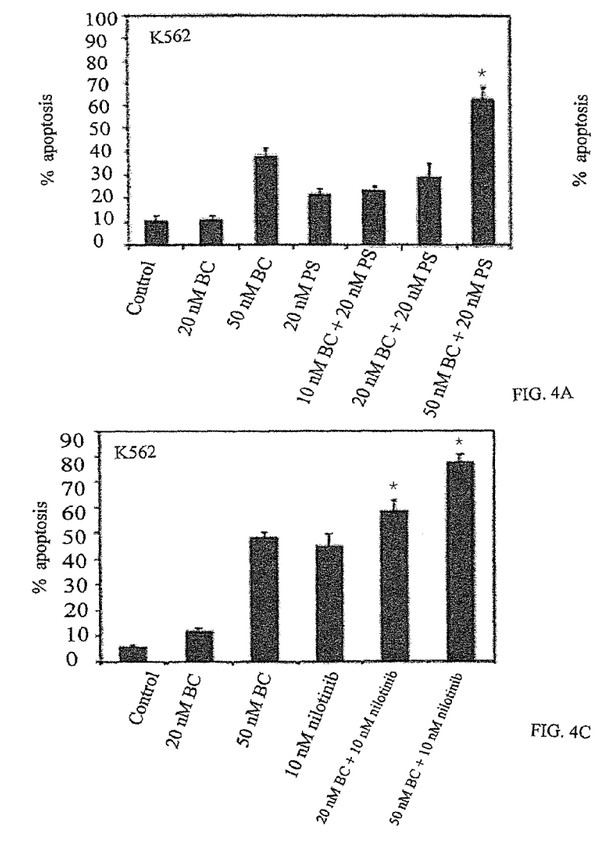
FIGS. 4A-4C are bar charts that depict the activity of Compound 1 on CML cells in inducing apoptosis in combination with other agents.
Figure 4B:
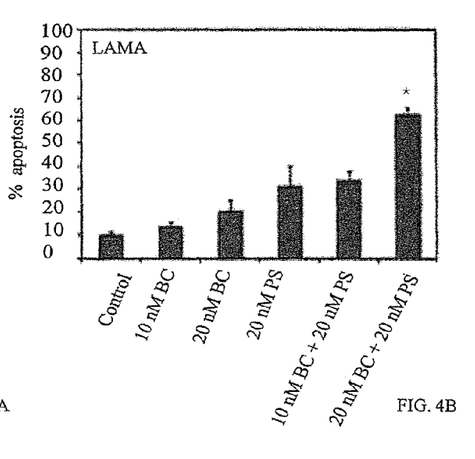

FIGS. 4A-4C are bar charts that demonstrate the results of this experiment. As these Figures show, treatment with Compound 1 increased the number of apoptotic cells in both K562 and LAMA-84 cell lines. Panobinostat and nilotinib enhanced the effects of Compound 1.

Example 5

Activity of Compound 1 in a Mouse Model of Human MPN. We Determined the In Vivo Anti-MPN Activity of Compound 1

Briefly, NOD-SCID mice were sub-lethally irradiated and HEL 92.1.7 cells were infused into the tail vein and MPN established. Mice were treated with 15 or 20 mg/Kg of Compound 1 administered b.i.w for three weeks via the tail vein. Animals were followed for survival after dosing stopped. As compared to the control, Compound 1-treated mice demonstrated significantly improved survival (p<001).

Example 6

Effect of Compound 1 on β-Catenin Expression and Nuclear Localization in AML Cells The purpose of this experiment was to analyze the effect of Compound 1 on β-catenin expression and nuclear localization in AML cells.

Figure 5A:
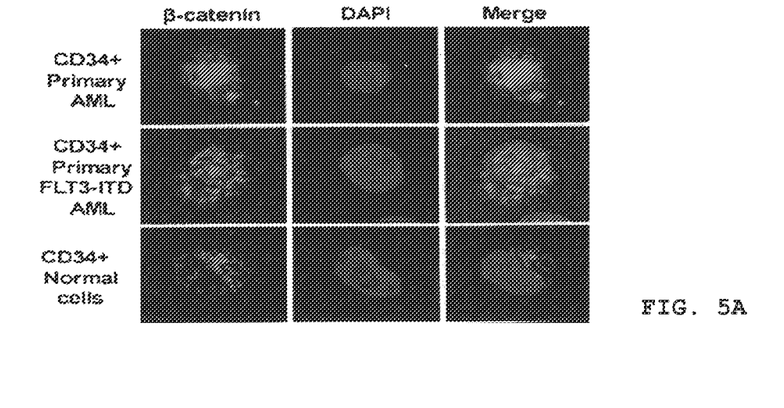
FIG. 5A is a series of photographs of CD34+ Primary AML cells, CD34+ Primary FLT3-ITD AML cells; and CD34+ normal AML cells.

Briefly, CD34+ Primary AML cells, CD34+ Primary FLT3-ITD AML cells and CD34+ Normal cells were stained with anti-β-catenin antibody and DAPI nucleic acid stain. The photographs of these stains were also merged. The photographs of the stained cells are contained in FIG. 5A. As these photographs show, there is a lot of β-catenin expressed in both types of AML cells, and β-catenin is concentrated in nuclei of these cells.

Figure 5B:
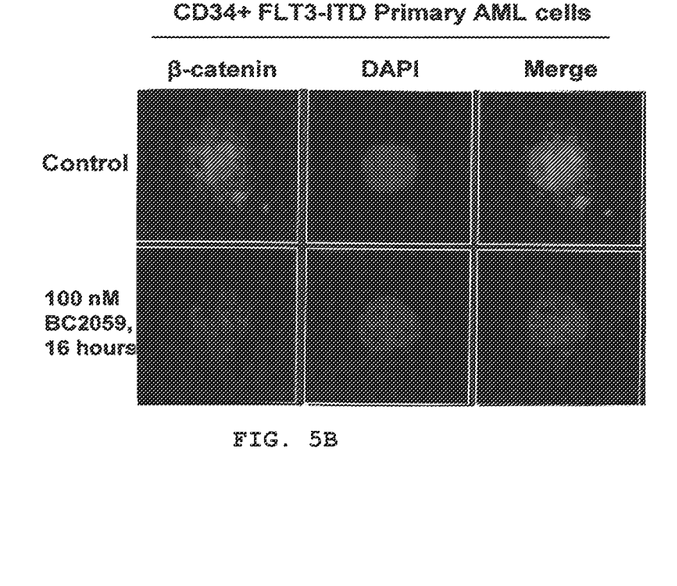
FIG. 5B is a series of photographs of CD34+ FLT3-ITD Primary AML cells in control conditions and 16 hours following the administration of Compound 1.

FIG. 5B demonstrates the results of treating CD34+ Primary FLT3-ITD AML cells with 100 nM of Compound 1 for 16 hours. As one can see, compared to control cells (i.e., not treated with Compound 1), this treatment leads to depletion of β-catenin expression and nuclear localization in AML cells.

Figure 5C:
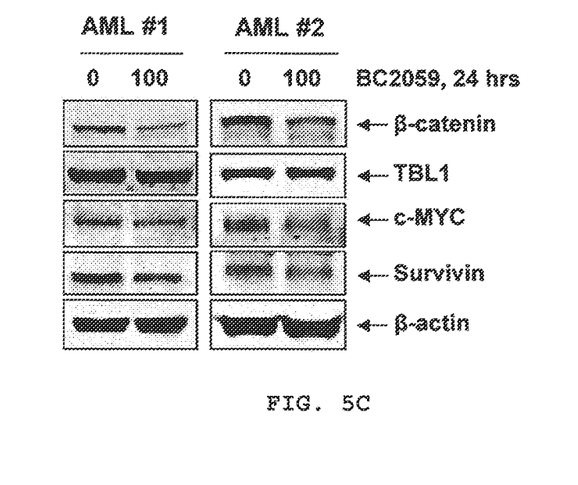
FIG. 5C is a photograph of the Western blot that depicts the effect of administration of Compound 1 on AML cells.

FIG. 5C is a photograph of the Western blot that further demonstrates that the treatment with Compound 1 leads to depletion of β-catenin expression and nuclear localization in AML cells. As one can see, the AML cells treated with 100 nM of Compound 1 expressed less of β-catenin, but about the same levels of TBL1, c-MYC, Survivin and β-actin.

Example 7

Effect of Compound 1 on Binding of β-Catenin to TBL1 in AML Cells

The purpose of this experiment was to analyze the effect of Compound 1 on binding of β-catenin to TBL1 in AML cells.

Figure 6A:
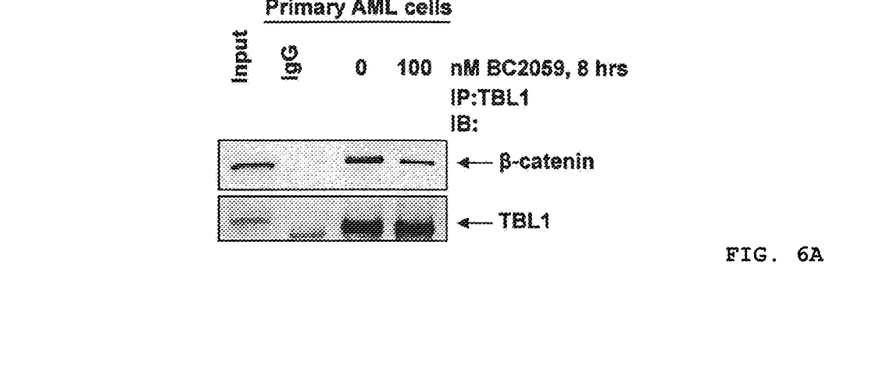
FIG. 6A is a photograph of the Western blot that demonstrates the effect of administration of Compound 1 on binding of β-catenin to TBL1 in primary AML cells.

FIG. 6A is a photograph of the Western blot that demonstrates that there is less of β-catenin in primary AML cells after they were treated with 100 nM of Compound 1 for 8 hours.

Figure 6B:
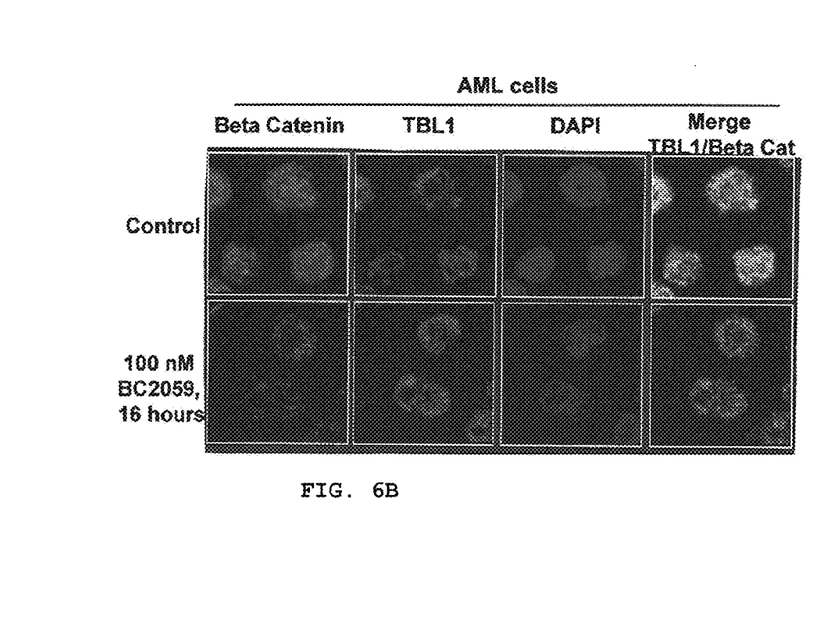
FIG. 6B is a series of photographs of stained AML cells with and without prior administration of Compound 1.

FIG. 6B is a series of photographs of stained AML cells with and without prior administration of Compound 1. The top panel depicts control cells (without prior administration of Compound 1) and the bottom panel depicts AML cells following administration of 100 nM of Compound 1 for 16 hours. The cells were stained with the anti-β-catenin antibody, anti-TBL1 antibody, and DAPI nucleic acid stain. The photographs of TBL1 and anti-beta-catenin stains were also merged. As one can see, administration of Compound 1 depleted the levels of β-catenin and severely disrupted binding of β-catenin to TBL1. Compare especially the top right photograph and the bottom right photograph.

Figure 6C:
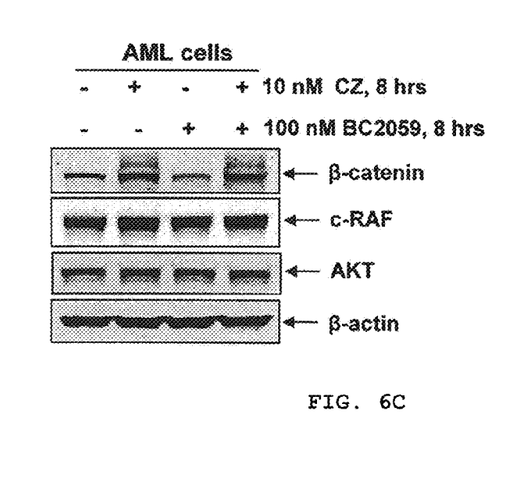
FIG. 6C is a is a photograph of the Western blot that demonstrates the effect of administration of Compound 1 on binding of β-catenin to TBL1 in AML cells.

FIG. 6C is a photograph of the Western blot that demonstrates that administration of Compound 1 to AML cells leads to proteasomal degradation of β-catenin. As one can see, there is less of β-catenin in the AML cells treated with 100 nM of Compound 1 for 8 hours as compared to non-treated AML cells. However, when 10 nM of Carfilzomib (CZ) (a proteasome inhibitor) were administered to the same AML cells, the amount of β-catenin increased.

Example 8

Effect of Compound 1 on β-Catenin at Target Gene Promoters and Transcription in AML Cells The purpose of this experiment was to analyze the effect of Compound 1 on β-catenin at target gene promoters and transcription in AML cells.

Figure 7A:
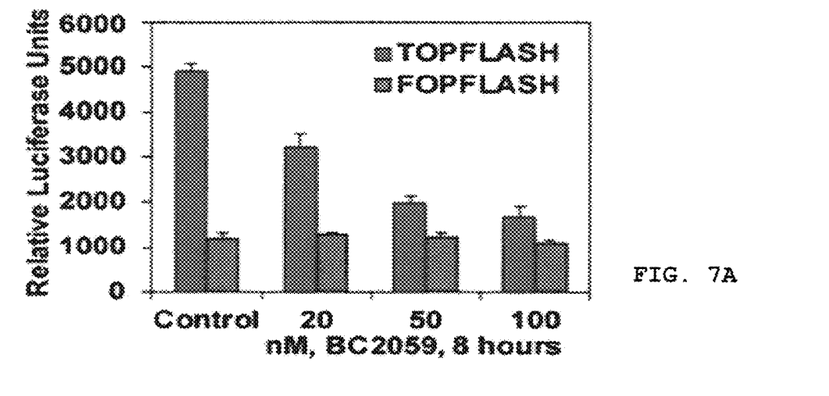
FIG. 7A depicts a bar chart of TOP-FLASH and FOP-FLASH luciferase activity versus treatment of AML cells with different amounts of Compound 1

FIG. 7A depicts a bar chart of TOP-FLASH and FOP-FLASH luciferase activity versus treatment of AML cells with different amounts of Compound 1.

TOP-FLASH is a Transfection grade T-cell factor (TCF) reporter plasmid containing two sets (with the second set in the reverse orientation) of three copies of the TCF binding site (wild type) upstream of the Thymidine Kinase (TK) minimal promoter and Luciferase open reading frame.

FOP-FLASH is a reporter plasmid containing mutated TCF binding sites is a negative control.

Figure 7B:
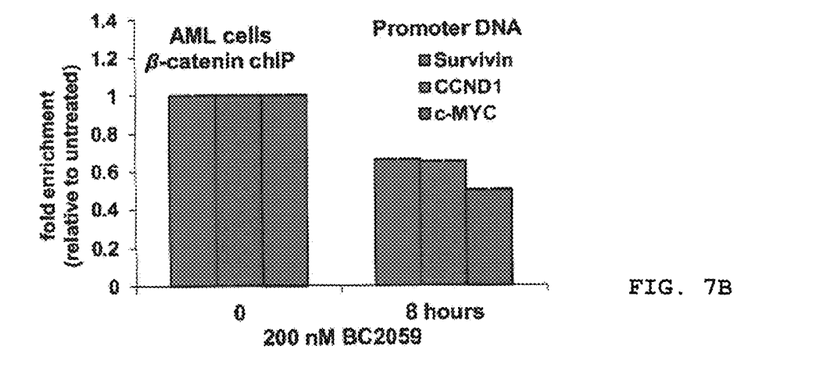
FIG. 7B contains the bar chart of the results of chIP (Chromatin immunoprecipitation) analysis of the effect of treating AML cells with Compound 1.

As FIG. 7A demonstrates, the treatment with 20 nM, 50 nM, and 100 nM of Compound 1 resulted in much lower expression of β-catenin as measured by this luciferase assay. There was no reduction in FOP-FLASH (negative control). These results indicate that treatment of AMC cells with Compound 1 results in reduced expression of β-catenin FIG. 7B contains the bar chart of the results of chIP (Chromatin immunoprecipitation) analysis of the effect of treating AML cells with Compound 1. As FIG. 7B shows, treatment of AML cells with 200 nM of Compound 1 for 8 hours resulted in reduced amount of promoter DNA of survivin, CCND1 and c-MYC.

Figure 7C:
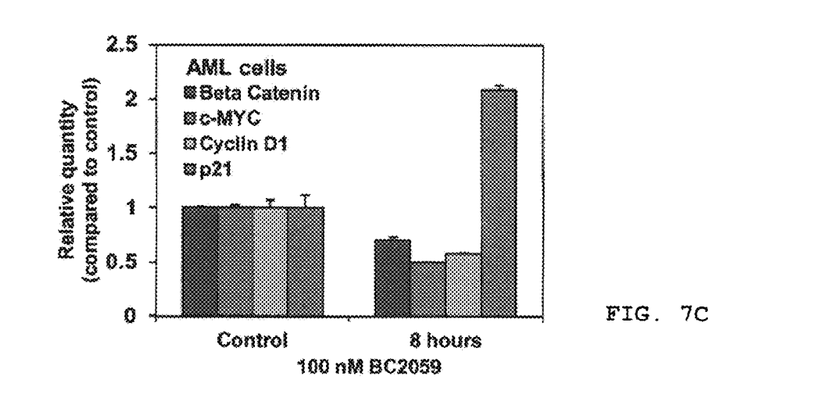
FIG. 7C contains the bar chart of the effect of administering 100 nM of Compound 1 to AML cells on levels of β-catenin, c-MYC, Cyclin D1 and p21 (control).

FIG. 7C contains the bar chart of the effect of administering 100 nM of Compound 1 to AML cells on levels of β-catenin, c-MYC, Cyclin D1 and p21 (control). As FIG. 7 demonstrates, the treatment with 100 nM of Compound 1 resulted in lower expression of β-catenin, c-MYC, and Cyclin D1, and much higher expression of p21.

Example 9

Effect of Compound 1 on In Vitro Apoptosis and Survival of NSG Mice Engrafted with Primary AML Cells The purpose of this experiment was to analyze the effect of Compound 1 on in vitro apoptosis and survival of NSG mice engrafted with primary AML cells.

Figure 8A:
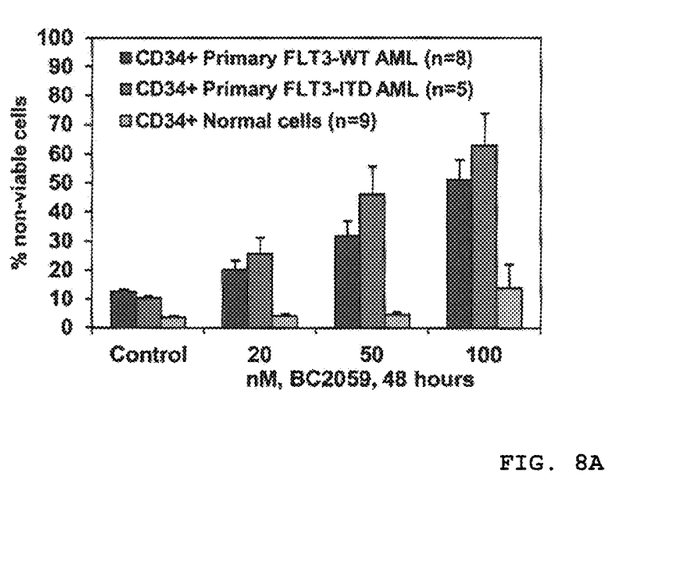
FIG. 8A is a bar chart that shows a % of non-viable cells in CD34+ Primary FLT3-WT AML cells, CD34+ Primary FLT3-ITD AML cells and CD34+ Normal cells treated with various amounts of Compound 1.

FIG. 8A is a bar chart that shows a % of non-viable cells in CD34+ Primary FLT3-WT AML cells, CD34+ Primary FLT3-ITD AML cells and CD34+ Normal cells treated with various amounts of Compound 1. As FIG. 8A demonstrates, Compound 1 significantly induced in vitro apoptosis in the both types of AML cells.

Figure 8B:
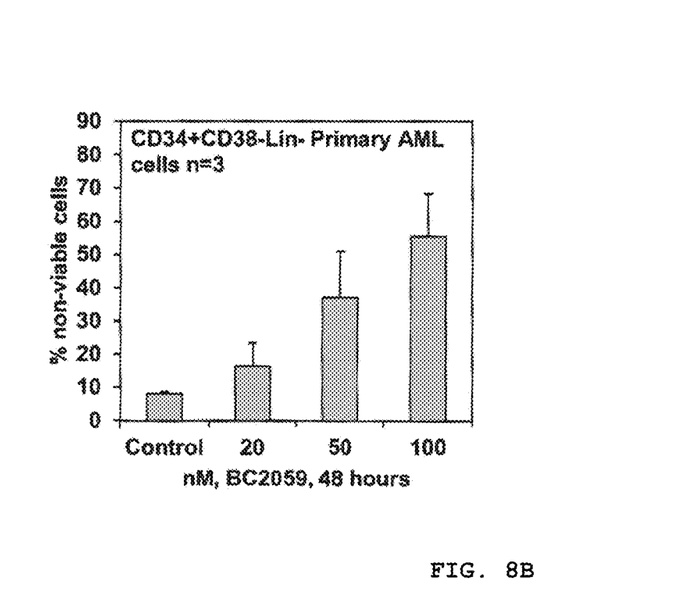
FIG. 8B is a bar chart that shows a % of non-viable cells in CD34+ CD38-Lin-Primary AML cells treated with various amounts of Compound 1.

FIG. 8B is a bar chart that shows a % of non-viable cells in CD34+ CD38-Lin-Primary AML cells treated with various amounts of Compound 1. As FIG. 8B demonstrates, Compound 1 significantly induced in vitro apoptosis in the AML cells.

Figure 8C:
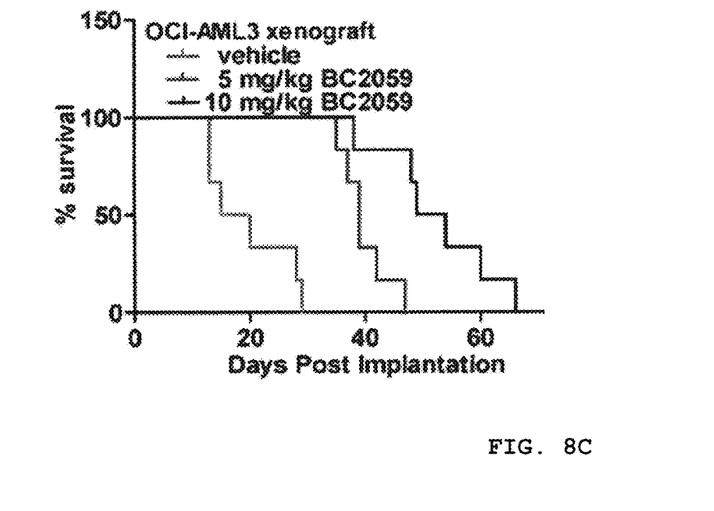
FIG. 8C is a chart that demonstrates the effect of treatment with Compound 1 on survival of NSG mice engraffed with OCI-AML3.

Treatment with Compound 1 for three weeks, twice per week tail vein infusion, in NOD-SCID-IL2γ receptor deficient (NSG) mice with established AML by OCI-AML3 xenograft cells resulted in improved survival as compared to the control mice. FIG. 8C contains a chart that demonstrates the results of this experiment. Both 5 mg/kg Compound 1 and 10 mg/kg Compound 1 treatments resulted in improved survival, with the 10 mg/kg dose being more effective.

Figure 8D:
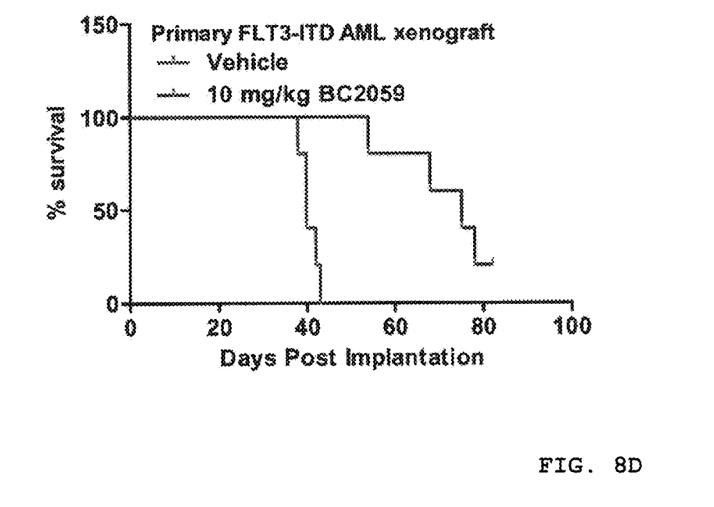
FIG. 8D is a chart that demonstrates the effect of treatment with Compound 1 on survival of NSG mice engraffed with Primary FLT3-ITD AML3.

Very similar results were obtained in NSG mice with primary FLT3-ITD AML xenograft. As shown in FIG. 8D, treatment with 10 mg/kg Compound 1 (three weeks, twice per week intravenous infusion) resulted in a dramatic increase in % survival as compared to the control mice.

These results strongly suggest that Compound 1 significantly improves survival of NSG mice engrafted with primary AML cells.

What is claimed is:

1. A method of modulating, ameliorating or stabilizing at least one physical parameter of a cancer, or a symptom thereof, and/or delaying the onset of a cancer, said cancer being from myeloproliferative neoplasia, chronic myeloid leukemia and acute myeloid leukemia, comprising administering to a patient in need thereof a therapeutically effective amount of a compound having the following structure:

2. A method of modulating, ameliorating or stabilizing at least one physical parameter of a cancer, or a symptom thereof, and/or delaying the onset of a cancer, said cancer being selected from myeloproliferative neoplasia, chronic myeloid leukemia and acute myeloid leukemia, comprising administering to a patient in need thereof a:

in combination with an agent that inhibits JAK2 kinase, BCR-ABL kinase, or histone deacetylase.

3. The method of claim 1, wherein the cancer is selected from myeloproliferative neoplasia.

4. The method of claim 1, wherein the cancer is selected from chronic myeloid leukemia.

5. The method of claim 1, wherein the cancer is selected from acute myeloid leukemia.

6. The method of claim 2, wherein the cancer is selected from myeloproliferative neoplasia.

7. The method of claim 2, wherein the cancer is selected from chronic myeloid leukemia.

8. The method of claim 2, wherein the cancer is selected from acute myeloid leukemia.

9. The method of claim 2, wherein an agent that inhibits JAK2 kinase is administered.

10. The method of claim 9, wherein the agent that inhibits JAK2 kinase is N-tert-butyl-3-[[5-methyl-2-[4-(4-methylpiperazin-1-yl)anilino]pyrimidin-4-yl]amino]benzenesulfonamide.

11. The method of claim 2, wherein an agent that inhibits BCR-ABL kinase is administered.

12. The method of claim 2, wherein an agent that inhibits histone deacetylase is administered.

13. The method of claim 1, wherein said cancer symptom is ameliorated.

14. The method of claim 1, wherein said cancer symptom is modulated.

15. The method of claim 1, wherein said cancer symptom is stabilized.

16. The method of claim 1, wherein the onset of said cancer is delayed.

17. The method of claim 2, wherein said cancer symptom is ameliorated.

18. The method of claim 2, wherein said cancer symptom is modulated.

19. The method of claim 2, wherein said cancer symptom is stabilized.

20. The method of claim 2, wherein the onset of said cancer is delayed.

* * * * *